United States Patent
Sandrin et al.

(10) Patent No.: US 8,663,111 B2
(45) Date of Patent: Mar. 4, 2014

(54) INSTRUMENT FOR MEASURING ORGAN ELASTICITY, OF THE TYPE COMPRISING A CENTRING MEANS

(75) Inventors: Laurent Sandrin, l'Hay-les-Roses (FR); Jean-Michel Hasquenoph, Couilly-Pont-aux-Dames (FR)

(73) Assignee: Echosens SA, Paris (FR)

( * ) Notice: Subject to any disclaimer, the term of this patent is extended or adjusted under 35 U.S.C. 154(b) by 1825 days.

(21) Appl. No.: 11/576,007

(22) PCT Filed: Sep. 28, 2005

(86) PCT No.: PCT/FR2005/002397
§ 371 (c)(1),
(2), (4) Date: Mar. 26, 2007

(87) PCT Pub. No.: WO2006/035160
PCT Pub. Date: Apr. 6, 2006

(65) Prior Publication Data
US 2008/0058644 A1    Mar. 6, 2008

(30) Foreign Application Priority Data

Sep. 28, 2004  (FR) .................................... 04 10265

(51) Int. Cl.
*A61B 8/00*    (2006.01)

(52) U.S. Cl.
USPC .......................................................... 600/438

(58) Field of Classification Search
USPC .......................................................... 600/438
See application file for complete search history.

(56) References Cited

U.S. PATENT DOCUMENTS

| | | | |
|---|---|---|---|
| 4,320,659 A * | 3/1982 | Lynnworth et al. ............. 73/589 |
| 4,881,549 A | 11/1989 | Rhyne | |
| 5,125,410 A * | 6/1992 | Misono et al. ................ 600/463 |
| 6,511,427 B1 * | 1/2003 | Sliwa et al. ................... 600/438 |
| 6,543,700 B2 * | 4/2003 | Jameson et al. ............ 239/102.1 |
| 7,135,809 B2 * | 11/2006 | Ossmann ....................... 310/335 |
| 2003/0073987 A1 * | 4/2003 | Sakurai et al. .................. 606/28 |
| 2003/0171678 A1 * | 9/2003 | Batten et al. .................. 600/443 |
| 2004/0006266 A1 | 1/2004 | Ustuner et al. | |
| 2004/0236223 A1 * | 11/2004 | Barnes et al. ................. 600/459 |
| 2005/0203398 A1 | 9/2005 | Sandrin et al. | |

\* cited by examiner

*Primary Examiner* — Tse Chen
*Assistant Examiner* — Hien Nguyen
(74) *Attorney, Agent, or Firm* — Stites & Harbison PLLC; Douglas E. Jackson

(57) ABSTRACT

The invention relates to an instrument for measuring the elasticity of a human or animal organ located behind the ribs. The instrument includes a casing having an actuator therein, the end of which is equipped with a transducer that is actuated in order to measure the elasticity of the organ. The measuring instrument also includes a mechanism for centering the transducer between the ribs.

15 Claims, 3 Drawing Sheets

INSTRUMENT FOR MEASURING ORGAN ELASTICITY, OF THE TYPE COMPRISING A CENTRING MEANS

This present invention concerns the area of measuring the visco-elastic properties of soft tissue.

This present invention more particularly concerns an instrument for measuring the elasticity of a human or animal organ located behind the ribs of the said human or animal.

It applies in particular, but not exclusively, to measuring the elasticity of the liver of a human or of an animal, the advantage of this measurement being that the latter is correlated with the quantity of fibrosis present in the liver. In fact chronic hepatitis, which can be of alcoholic, viral or other origin, produces a fibrosis effect that it is important to ascertain, in order to choose the best moment at which to treat this disease.

Prior art has already included such measuring instruments.

Previously proposed in fact, in international patent application WO 2004/016176, submitted by the present applicant, has been a device for measuring the elasticity of a human or animal organ, including at least one feeler mechanism consisting of an ultrasound transducer, at least one position sensor, and a controlled electrodynamic actuator fixed to the ultrasound transducer and capable of generating a transient low-frequency pulse. The low-frequency pulse transmitted by the ultrasound transducer leads to the propagation in the tissues of an elastic wave whose speed depends on the elasticity of the medium.

However, such a device has certain drawbacks, in particular when it concerns measuring the elasticity of organs located behind the ribs of a human being or an animal, such as the liver.

In fact, in order to measure the elasticity of these organs, the device is placed in front of the thoracic cage, with the free end of the transducer being placed between two adjacent ribs (the intercostal space). However, the positioning of the transducer in the intercostal space, but also its retention when the latter is moved in this same intercostal space, remains relatively difficult. There is therefore a certain probability that the end of the transducer takes up position not in the intercostal space, but directly on a rib, when it then generates invalid measurements.

Moreover, the perpendicular positioning of the transducer axis in relation to the surface of the skin, which is necessary in order to obtain good transmission of the low-frequency elastic waves and the ultrasound waves, cannot always be guaranteed.

Furthermore, in order that the low-frequency elastic wave emitted by the vibrating ultrasound transducer can pass through the skin of the human being or animal and reach the organ to be measured, it is necessary to exert a sufficient pressure of the device against the latter. This is all the more true for very overweight patients. In the aforementioned device, the pressure exerted is directly borne by the transducer, and therefore by the electrodynamic actuator on which it is fixed, possibly leading to a reduction in the quality of the vibration.

This present invention is intended to remedy the drawbacks of previous designs by proposing a measuring instrument that allows the transducer to be guided between two adjacent ribs in order to prevent the latter from being directly in contact with one of the said ribs.

This present invention also has as its objective to allow the sliding of the measuring instrument along the intercostal space.

This present invention also has as its objective to ease the work of the practitioner, with the weight of the measuring instrument being partially taken by the human or the animal.

Furthermore, this present invention has as its purpose to offer improved transmission of the vibration by reducing the phenomenon of recoil of the measuring instrument during the shock associated with the emission of the low-frequency elastic wave by the measuring device.

This present invention also aims to propose a measuring instrument that allows to increase the gap between two adjacent ribs. Such an instrument will therefore have a particular advantage for those patients who have a narrow intercostal space.

This present invention also aims to propose a measuring instrument that can be adapted to the morphology of the patient.

This present invention also has as its objective to propose a measuring instrument that reduces the pressure sustained by the electrodynamic actuator.

This present invention also has as its objective to improve the perpendicular positioning of the transducer axis in relation to the surface of the skin.

To this end, this present invention concerns an instrument for measuring the elasticity of a human or animal organ located behind the ribs of the said human or animal, the said measuring instrument being composed of a low frequency elastic wave generator and a transducer designed to be operated so as to measure the elasticity of the said organ. It is characterised in that, in its broadest interpretation, the measuring instrument also includes a means for centring the transducer between the ribs.

This centring means preferably includes at least two locating posts provided on either side of the transducer.

Advantageously, the said locating posts have transverse dimensions that allows the said locating posts to be pressed against the ribs.

Advantageously, the said locating posts are of rounded shape.

According to a preferred method of implementation of the invention, the centring means is formed of a ring fixed to the casing, where the said ring includes a hole in which the said transducer is positioned.

Advantageously, the ring consists of an annular crown on which the said locating posts are positioned in a diametrically opposed manner. Advantageously, the ring is fixed to the casing by means of springs.

Advantageously, the ring is removable.

According to a variant of the invention, the centring means is composed of one or more pressure sensors.

According to another variant of the invention, the centring means is composed of one or more ultrasound transducers. According to another particularly advantageous variant of the invention, the centring means includes at least one imagery transducer that allows the formation of an echographic image of the said organ. More particularly, at least one of the locating posts forming the centring means is composed of a wall that is transparent to the ultrasound, with the said wall forming a cavity in which the imagery transducer is housed.

Thus when measuring the elasticity of the organ under investigation, the operator is able to locate this organ by the display of a corresponding echographic image.

Preferably, the imaging transducer is a one of the single-element type. In order to allow the formation of echographic images, such a transducer is then hinged onto the said instrument on the transverse pivotal axis.

Advantageously, the said transducer is motor-driven.

In order to facilitate the passage of the ultrasound from the imagery transducer in the direction of the wall of the associated locating post, the cavity is filled with a coupling liquid. Advantageously, the cavity includes a sealing membrane intended to prevent the liquid from flowing into the electronic parts of the measuring instrument (the motor controlling the transducers, etc.). The coupling liquid is thus retained in the cavity by the sealing membrane. Advantageously, the sealing membrane is a flexible membrane in order to allow the pivoting of the imagery transducer in the cavity.

According to a particular method of implementation of the invention, the measuring instrument also includes a protective membrane covering the distal end of the said measuring instrument, this distal end being formed by the transducer and the centring means.

Advantageously, the means for generating the low-frequency elastic wave is formed by the transducer or the centring means.

Likewise, in an advantageous method of implementation of the invention, the measuring instrument includes a heating device that is used to heat the said centring means. When thus heated by means of the centring means, the skin offers better propagation of the ultrasound waves.

The invention will be understood better on reading the description provided below, purely for explanatory reasons, with reference to the appended figures, in which:

FIG. 1 illustrates an instrument 1 for measuring the elasticity of a human or animal organ, according to a first method of implementation of the invention.

Figure 1:
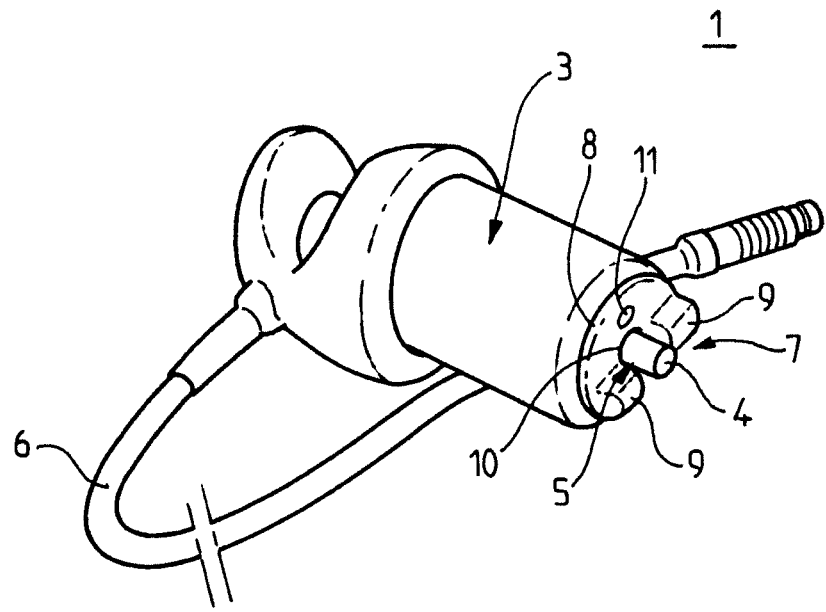
FIG. 1 illustrates a view in perspective of a measuring instrument according to a first method of implementation of the invention.

The said measuring instrument 1 is intended in particular to measure the elasticity of a human or animal organ located behind the ribs 2 of the said human or animal.

The said measuring instrument 1 has a casing 3 in which an electrodynamic actuator (not shown) is housed. At the end of the actuator is mounted a mobile ultrasound transducer 4 in which a part of the distal end 5 extends outside the body 3 of the said the measuring instrument 1. The measuring instrument 1 is also connected to an energy source by a wire link 6.

Since the purpose of the invention is to improve an already existing measuring instrument (a measuring instrument described in patent application WO 2004/016176, we will not endeavour to describe its structure in any greater detail. For the creation of the said measuring instrument 1, as well as for the comprehension of its operation, the professional engineer should refer to international patent application WO2004/016176. However, it is quite obvious of course that here this configuration of the measuring instrument is provided purely for explanatory purposes. Other configurations can be envisaged by a professional engineer without going outside the context of the invention. In particular, it is possible to envisage a measuring instrument that does not have an actuator, the function of the said actuator being taken on directly by the said transducer for example.

In order to allow the positioning and the retention of the distal end 5 of the transducer 4 between two adjacent ribs, the said measuring instrument 1 includes a means 7 for centring the transducer 4 between the ribs.

The centring means 7, illustrated in FIG. 1, consists advantageously of a ring 8 fixed to the casing 3, with the free side of the said ring 8 presenting two locating posts 9. The said ring 7 includes a hole 10 so that, when the ring is fixed to the said casing 3, the distal end 5 of the said transducer 4 passes through the hole 10 formed in the said ring 8.

In the implementation example illustrated in FIG. 1, the ring 8 is fixed to the said measuring instrument 1 by means of a screw 11. It is quite obvious here of course that the present invention is not limited to this attachment method only. The ring 8 could, for example, be configured to clip onto the said measuring instrument 1 preferably in a reversible manner.

But whatever the method, the said ring 8 will preferably be removable. Thus, depending on the morphology of the patient, it will only be necessary to change the ring 8 in order to obtain a measuring instrument 1 whose centring means 7 are suitable for the intercostal space of the patient being examined (adaptation of the locating posts for example, in terms of height or of transverse dimensions). Advantageously, the hole 10 is positioned at the centre of the said ring 8.

Advantageously, the two locating posts 9 are positioned in a diametrically opposed manner on either side of the hole 10, which is traversed by the distal end 5 of the transducer 4.

Advantageously, the said locating posts 9 constitute pressure sensors or ultrasound transducers.

Figure 4:
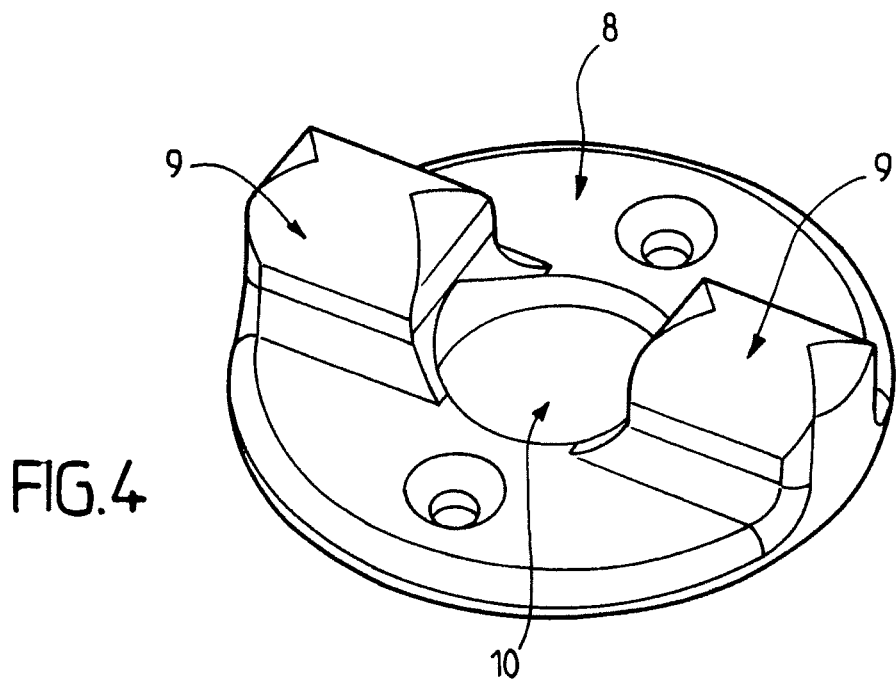
FIG. 4 illustrates a view in perspective of the means for centring the said measuring instrument of FIG. 1.

FIG. 4 more clearly illustrates the shape and the structure of such a ring.

Figure 2:
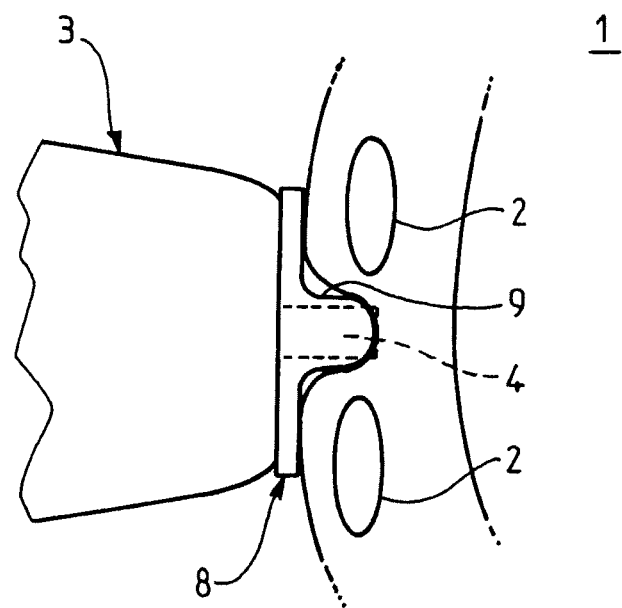
FIG. 2 illustrates a partial side view in section of the measuring instrument of FIG. 1.

FIG. 2 illustrates a partial side view of the measuring instrument 1 when the latter is positioned against the thoracic cage of a patient.

More particularly, when the measuring instrument 1 is placed against the thoracic cage, the locating posts 9 of the ring 8 are such that they takes up position in the space 11 formed between two adjacent ribs 2, thus placing the distal end 5 of the transducer 4 in the intercostal space 11.

As explained earlier, it is necessary, in order to allow measurement of the elasticity of an organ, to maintain the measuring instrument 1 against the thoracic cage with a certain pressure, in order that the waves should be transmitted correctly through the skin of the patient. Since locating posts 9 are also intended to prevent this pressure from being borne only by the transducer 4, the height of the locating posts 9 is determined so that they should be in contact with the skin when the pressure exerted is sufficient in order to allow correct transmission of the low-frequency waves through the skin of the patient, and therefore in order to allow the examination to be performed.

In addition, the locating posts 9 advantageously have transverse dimensions that allow them to be pressed against the ribs 2 between which they are positioned.

Advantageously, the said locating posts 9 are of rounded shape so that, when the measuring instrument 1 is pressed against the thoracic cage, they cause no injury to the patient.

In order to further reduce this risk of injury, the locating posts 9 will advantageously be made of a deformable material (rubber, etc.). Thus, not only will the pressure exerted on the surface of the skin by the said locating posts 9 be better distributed, but also the shock associated with the emission of the low-frequency elastic wave by the transducer 4 will be damped. Likewise, the ring 8 can also be fixed to the casing 3 of the said measuring instrument 1 by means of elements forming a spring (not shown).

According to one particular configuration of the invention, the measuring instrument 1 also includes a protective membrane covering the ring 8. The function of this membrane is not only to protect the measuring instrument 1 from being fouled, in particular by the application of a gel favouring the transmission of the waves, but also to prevent contamination passing from one patient to another by the use of a fresh membrane for each new operation on a patient.

Advantageously, the said membrane includes echographic gel in order to ensure correct ultrasound coupling.

Furthermore, in order to prevent contamination passing from one patient to another, the said ring 8 is advantageously disposable.

Figure 3:
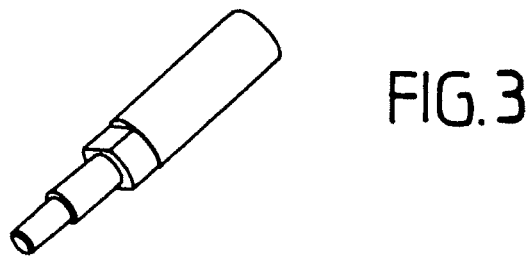
FIG. 3 illustrates a view in perspective of the transducer used with the measuring instrument of FIG. 1.

Concerning the transducer 4 of the measuring instrument 1 illustrated in FIG. 1, the latter is a transducer of the circular type. It is presented in its entirety in FIG. 3. This configuration of the transducer is provided here by way of example only. It is quite obvious of course that any transducer of a shape other than circular could be used equally well.

Figure 5:
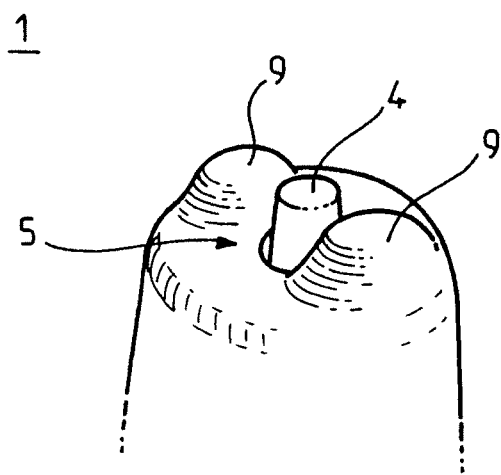
FIG. 5 illustrates a view in partial perspective of a measuring instrument according to a second method of implementation of the invention.

FIG. 5 illustrates a view in partial perspective of a measuring instrument according to a second method of implementation of the invention. In this method of implementation, the end of the measuring instrument 1 intended to be in contact with the thoracic cage of the patient has two locating posts 9 forming the means for centring the transducer 4 between the ribs. The said locating posts 9, as in the method of implementation of the measuring instrument described previously, are positioned on either side of the distal end 5 of the transducer 4 extending outside of the casing 3.

As before, the measuring instrument 1 is advantageously equipped, at the end with the locating posts 9, with a protective membrane designed to protect the transducer from any contamination during its contact with the surface of the skin of the human being or animal.

Figure 6:
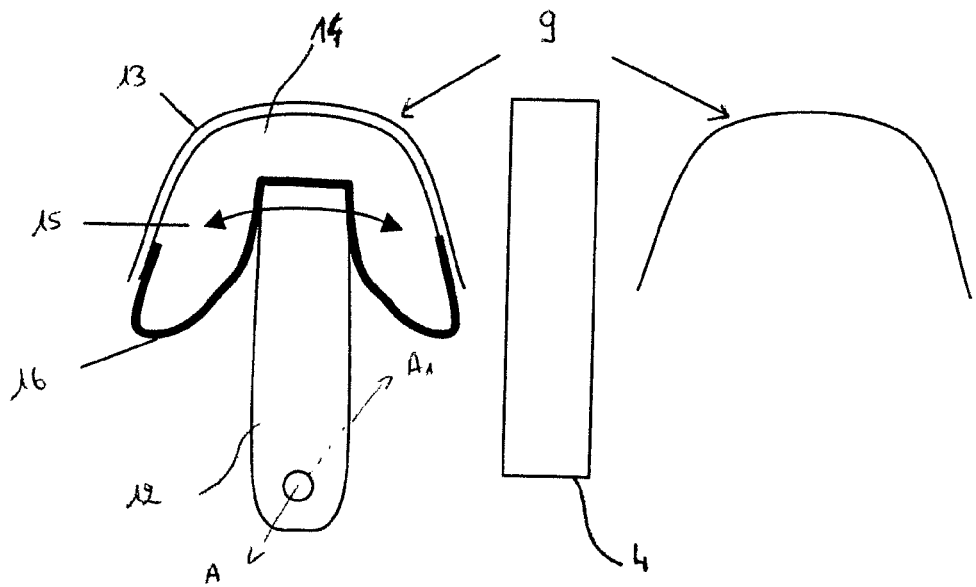
FIG. 6 illustrates a detailed view of a means for centring a measuring instrument according to a particular method of implementation of the invention.

FIG. 6 illustrates a particularly advantageous configuration of the locating posts 9 forming the centring means 7 of the said measuring instrument 1, with the said locating posts 9 being positioned on either side of the transducer 4 intended to measure elasticity.

The said locating posts 9 are respectively composed of a wall 13 forming a cavity 14 within which is housed an imagery transducer 12.

Preferably, the imagery transducer 12 is one of the single-element type. In order to allow the formation of echographic images, such a transducer is hinged onto the said instrument 1 on the transverse pivotal axis AA1.

Advantageously, the said transducer is motor-driven.

It is quite obvious here of course that the professional engineer will be able to use transducers of the multi-element echographic bar type. However, the use of single-element transducers has the advantage of a lower implementation cost of the said measuring instrument 1 due to the fact that only one electronic acquisition path, combined with a multiplexer, is only necessary to sequentially control the single-element transducers making up the measuring instrument 1, namely the transducer 4 intended to measure the elasticity of the organ examined, and the imagery transducer 12.

Figure 7:
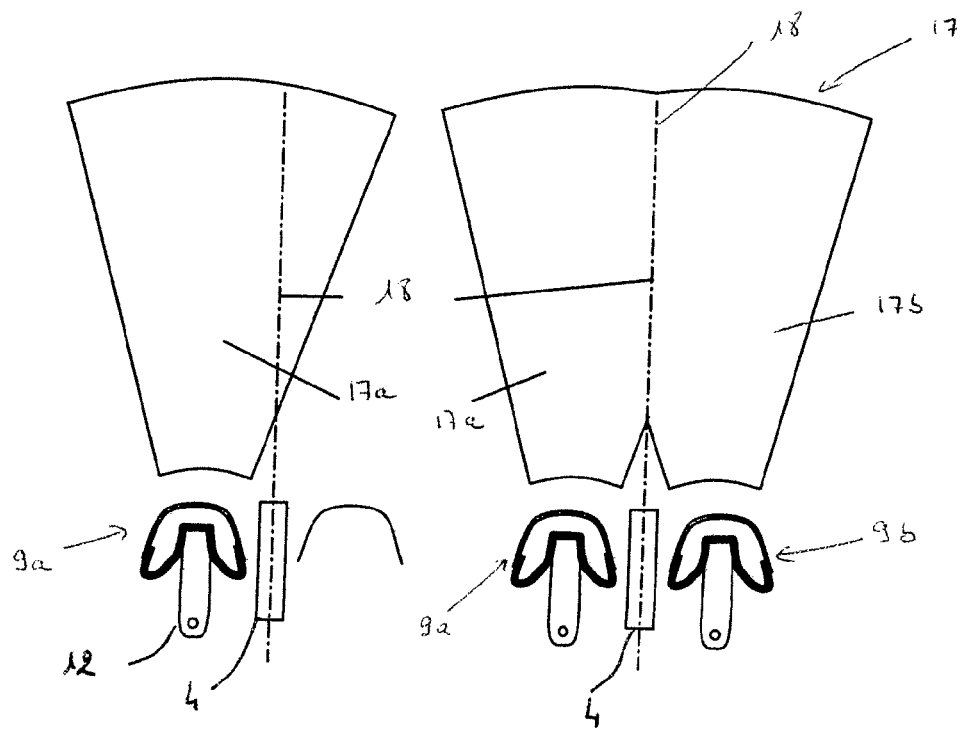
FIG. 7 illustrates the operation of a measuring instrument equipped with the centring means illustrated in FIG. 6.

Thus when measuring the elasticity of the examined organ, the operator is able to navigate within this organ by the display of a corresponding echographic image as illustrated in FIG. 7. The transducer 12a, 12b in each of the locating posts 9a, 9b sweeps its respective zone 17a, 17b of the organ, so that the total zone 17 swept by the said imagery transducers 12 covers the axis 18 of the elasticity measurement effected by the transducer 4.

Furthermore, in order to facilitate the passage of the ultrasound from the imagery transducer 12 in the direction of the wall 13 of the associated locating post 9, the cavity 14 is filled with a coupling liquid 15. The electronic parts of the said measuring instrument 1, and in particular the motor actuating the pivoting of the imagery transducer 12, are then protected by the positioning of a sealing membrane 16 in the cavity 14. The said membrane 16 is positioned in the cavity 14 so that the coupling liquid 15 is held against the wall 13, and more particularly against the upper wall of the locating post 9.

In the foregoing, the invention is described by way of an example only. It is intended that the professional engineer should be capable of creating different variants of the invention without going outside the scope of the patent.

The invention claimed is:

1. An instrument for measuring an elasticity of a human or animal organ located behind the skin and ribs of the human or animal, said instrument comprising:
    a casing,
    an actuator in said casing which generates a low-frequency elastic wave,
    a transducer including a transducer distal end which said transducer distal end extends longitudinally from said casing and which transmits the low-frequency elastic wave generated by said actuator into the skin of the human or animal towards the organ, said transducer also being designed to measure the elasticity of the organ using the low-frequency elastic waves entering the skin, and
    a means for centering the distal end of the transducer laterally between the two adjacent ribs, said centering means
        having a centering distal end located laterally adjacent the transducer distal end, whereby during use said centering distal end and said transducer distal end are both located in contact with the skin and pressed between the adjacent ribs whereby said transducer distal end is properly centered for transmitting the low-frequency elastic wave and for effecting the elasticity measurement of the organ,
        including at least two locating posts provided on either side of the distal end of the transducer, each said locating post having a respective said centering distal end, and
        having at least one of the locating posts including an imagery transducer, with the at least one locating post being composed of a wall that is transparent to ultrasound, forming a cavity in which the imagery transducer is housed.

2. A measuring instrument according to claim 1, wherein said transducer distal end includes opposed transducer centering sides which are also pressed laterally against the ribs through the skin.

3. A measuring instrument according to claim 1, wherein said locating posts are of rounded shape.

4. A measuring instrument according to claim 1, wherein the centering means includes a replaceable ring fixed to the casing, with said ring including a hole through which said transducer distal end extends.

5. A measuring instrument according to claim 4, wherein the replaceable ring consists of an annular crown on which first and second locating posts are provided, each said locating post having a said centering distal end, and said first and second locating posts being positioned in a diametrically opposed manner with said transducer therebetween.

6. A measuring instrument according to claim 4, wherein the ring is removable and replaceable with a different ring with a different centering means.

7. A measuring instrument according to claim 1, wherein the centering means is composed of at least one pressure sensor.

8. A measuring instrument according to claim 1, wherein the centering means is composed of at least one ultrasound transducer.

9. A measuring instrument according to claim 1, wherein the imagery transducer, of the single-element type, is hinged onto said casing on a transverse pivotal axis.

10. A measuring instrument according to claim 1, further including a motor that operates the pivoting of said imagery transducer.

11. A measuring instrument according to claim 1, wherein the cavity contains a coupling liquid, which is retained in the cavity by a sealing membrane.

12. A measuring instrument according to claim 1, further including a deformable protective membrane covering the centering and transducer distal ends.

13. A measuring instrument according to claim 1, wherein the actuator is formed by the transducer.

14. A measuring instrument according to claim 1, wherein the actuator is formed by the centering means.

15. A measuring instrument according to claim 1, further including a heating device to heat said centering means.

* * * * *